United States Patent [19]

Cooper

[11] Patent Number: 4,756,713
[45] Date of Patent: Jul. 12, 1988

[54] ARTIFICIAL KNEE

[75] Inventor: John E. Cooper, Leatherhead, United Kingdom

[73] Assignee: J. E. Hanger & Company Limited, London, United Kingdom

[21] Appl. No.: 917,976

[22] Filed: Oct. 14, 1986

[30] Foreign Application Priority Data

Oct. 14, 1985 [GB] United Kingdom ............... 8525303

[51] Int. Cl.$^4$ ............................................. A61F 2/64
[52] U.S. Cl. ....................................... 623/44; 623/39; 623/43; 16/326; 16/332
[58] Field of Search ................... 623/18, 19, 20, 21, 623/39, 43, 44, 41; 16/326, 333, 349

[56] References Cited

U.S. PATENT DOCUMENTS

| 688,936 | 12/1901 | Devol | 623/44 |
| 1,661,113 | 2/1928 | Deshon | 16/326 |
| 3,837,010 | 9/1974 | Prout | 623/43 X |

FOREIGN PATENT DOCUMENTS

| 1191301 | 8/1985 | Canada | 623/20 |
| 3414869 | 10/1985 | Fed. Rep. of Germany | 623/41 |
| 0543945 | 9/1922 | France | 16/326 |
| 0712942 | 8/1954 | United Kingdom | 623/43 |
| 0016268 | 10/1980 | United Kingdom | 623/39 |

OTHER PUBLICATIONS

Noiles Total Knee Prosthesis; 12/20/1979; page cover & 5.

Primary Examiner—Richard J. Apley
Assistant Examiner—Howard Flaxman
Attorney, Agent, or Firm—Shoemaker and Mattare, Ltd.

[57] ABSTRACT

A compact and lightweight knee joint for a prosthetic leg that can be locked or released with low operating forces comprises upper and lower members interconnected by a pin at a posterior location. A latch pivoted to one of the members for rotation about a vertical axis releasably locks into a recess in the other member to hold the joint in its extended position. The upper member has depending cheeks between which a head of the lower member is received. Adjoining horizontal faces of the upper and lower members are planar and a pad of elastomeric material attached to one of the planar surfaces serves as an extension stop buffer. The latch is blade-like and of bell-crank shape. It fits into slots in the anterior edge of each cheek and is pivoted in one of the slots with an anterior lever thereof spanning between the slots and with a latch head thereof fitting into the other slot. A cable release is fitted to the medial/lateral lever for release of the latch. The cable passes through a bore in the pin and an internal spring urges the latch towards its locking position.

6 Claims, 4 Drawing Sheets

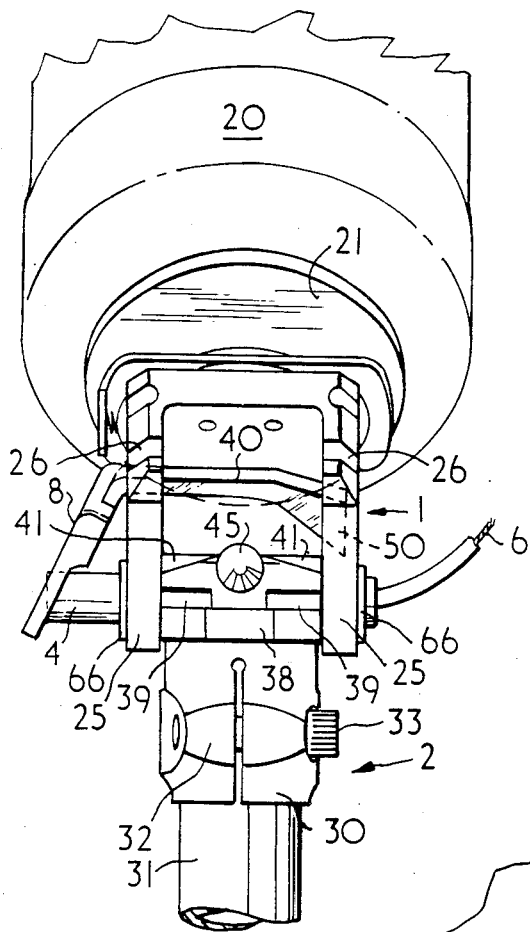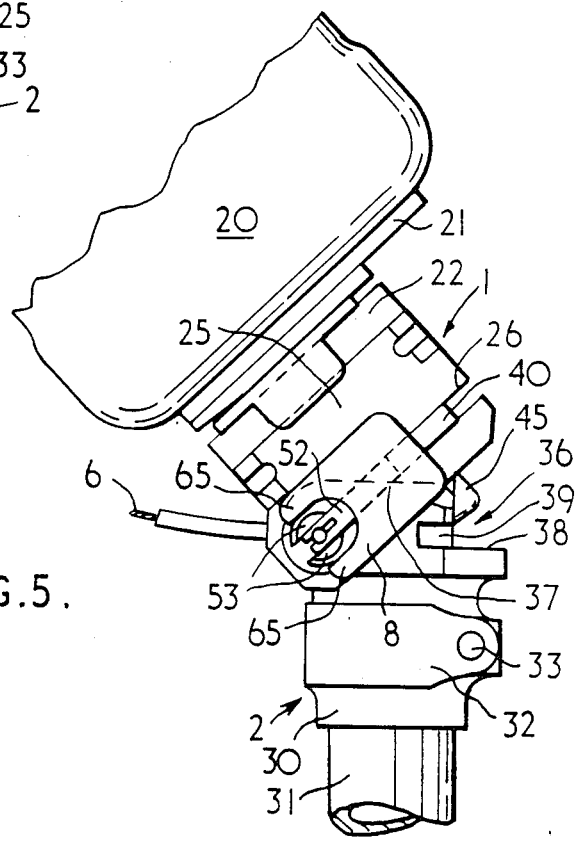

ARTIFICIAL KNEE

FIELD OF THE INVENTION

This invention relates to a knee joint for a leg prosthesis. In this specification the terms "vertical" and "horizontal" are general terms to be understood with reference to the attitude of the leg when the user is standing with his knees straight or extended.

BACKGROUND TO THE INVENTION

A representative self-locking knee joint of the prior art is shown in Patent Specification No. GB-B-2099708 and employs a sliding locking plunger pulled along its vertical line of action by a release cable, an upper member or knee ball being received in a housing forming part of the lower or shin member, and the knee pivot being between bearings to opposed sides of the knee housing. A similar joint in which a head of a lower memver fits between bifurcations of an upper member with a pin positioned at a posterior location is shown in U.S. Pat. Nos. 4,149,280 and 4,283,800 (Wilson), but there is no provision for locking the joint in extension.

SUMMARY OF THE INVENTION

It is an object of the invention to provide a knee joint for a leg prosthesis that is of light weight, is compact, is strong and is of low height considered with reference to the longitudinal direction of the leg and gives a large angle of flexion.

It is a further object of the invention to provide a knee joint for a leg prosthesis that locks and unlocks with low operating forces so that it can be used by elderly and arthritic patients.

It is a yet further object of the invention to provide a a knee joint for a leg prosthesis that when fitted into a cosmesis gives good cosmetic restoration and minimizes damage to foam of said cosmesis flowing from repeated flexion and extension of the knee.

Broadly stated the invention provides a knee joint for a leg prosthesis, wherein a pin at a posterior location of said joint pivotally interconnects upper and lower members, and a latch member pivoted to one of said members for rotation about a vertical axis releasably locks in a recess in the other of said members to hold the joint in its extended position.

DESCRIPTION OF PREFERRED FEATURES

The upper member preferably has depending medial and lateral portions defining cheeks between which a head of the lower member is received. The adjoining horizontal faces of the upper and lower members may be planar, in which case a pad of elastomeric material may be attached to one of said planar surfaces to act as an extension stop buffer. Advantageously the latch member is a generally bell-cranked blade, that fits into slots in the anterior edge of each cheek and is pivoted to one of the cheeks with an anterior lever spanning between the cheeks and having a latch head that fits into said socket and a medial/lateral lever actuated by a cable release. The lower member preferably has at an anterior position on its head a nose of wear resistant material that cams the blade to its release position as the joint moves to the extended position, the blade disengaging from the nose as the extended position is reached to snap into the recess. The release cable advantageously passes to a posterior portion of the medial/lateral lever through an axial bore in the pin, an enlarged portion of said bore housing a compression coil spring that urges the blade towards its locking position, and the posterior portion of the medial/lateral lever advantageously slides between furcations at an end of the pin during travel of the blade between release and locking positions.

BRIEF DESCRIPTION OF THE DRAWINGS

An embodiment of the invention will now be described, by way of example only, with reference to the accompanying drawings, in which:

FIGS. 5 and 6 are views corresponding to FIGS. 1 and 2, but with the knee joint flexed.

DETAILED DESCRIPTION OF PREFERRED EMBODIMENT

Figure 1:
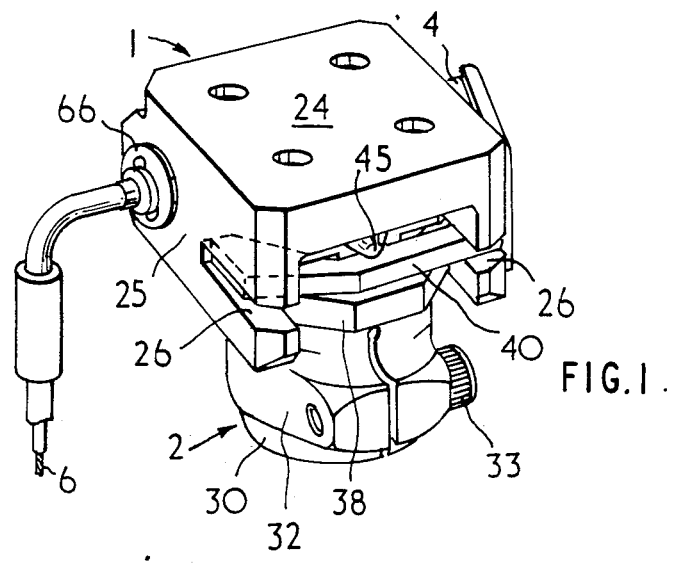
FIGS. 1 and 2 are respectively a front perspective view of a knee joint according to the invention in an upright unflexed position and laid flat in a partly flexed position and partially exploded.

In the drawings, a socket alignment cup 20 as described in assignee's pending UK patent application No. 8524028 is connected through baseplate 21 and optional socket rotator 22 as described in said patent application No. 8524028 to an upper knee joint assembly generally indicated by the reference numeral 1. The assembly 1 includes a body formed with portions defining a top plate 24 that is a mitered square in plan and has medial and lateral cheek plates 25. Each cheek plate 25 is formed with a narrow horizontal slot 26 extending in a posterior direction from the front edge of the plate and with a through-hole for a knee-joint pin 4 in a protruding part hexagonal posterior region 27 thereof.

A knee joint lower sub-assembly generally indicated by the reference numeral 2 has a depending socket 30 which fits onto the upper end of a shin tube 31. The tube 31 which may be of metal or carbon fibre is reinforced by a flanged metal tube slidingly fitted into its blind end, and in the illustrated arrangement which is for a carbon fibre tube the socket 30 is formed with a pinch bolt structure 32 that may be tightened by clamping bolt 33 to retain the tube 31 in the socket 30. Above the socket 30 the lower sub-assembly 2 is formed with an enlarged plate-like head 26 that fits between the cheek plates 25 of the upper knee-joint sub-assembly 1, the posterior portion of the head 36 being semi-circular in side profile and having a transverse bore into which the knee joint pin 4 fits. The head has a flat top surface 37 and an anterior cut-out defining a front step 38 bounded by medial and lateral recess or catch-defining cut-outs 39 of the same depth as a latch blade 40 that fits into and spans between the slots 26 of the upper assembly 1. The top face 37 is formed with medial and lateral downwardly bevelled surfaces 41 over which the blade 40 travels as the joint is unflexed before it engages in the catches or recesses 39. In the centre of the stepped front face of the head 36 there is a bullet-shaped nose 45 of wear-resistant material that serves to cam the blade 40 to its unlatched positon as the joint is unflexed, the blade snapping into one of the recesses 39 as the joint reaches its extend edposition. A flat top surface 37 of the head 26 has attached thereto, e.g. by fixing screws, a buffer stop 19 of elastomeric material with optional shim plates beneath it to adjust thee height of the stop 19 and properly define the unflexed position of the joint.

Figure 2:
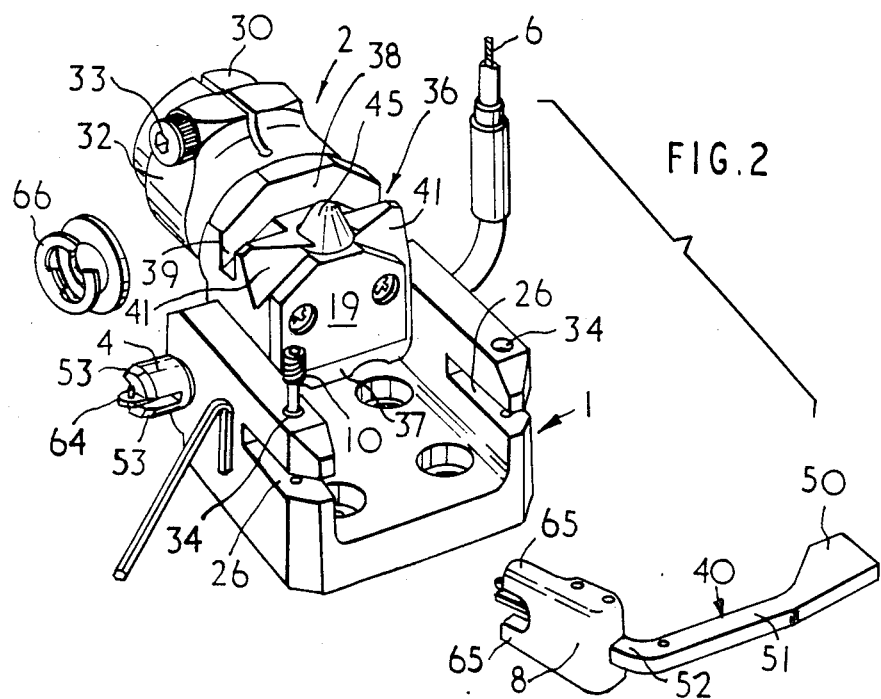
Figure 8:
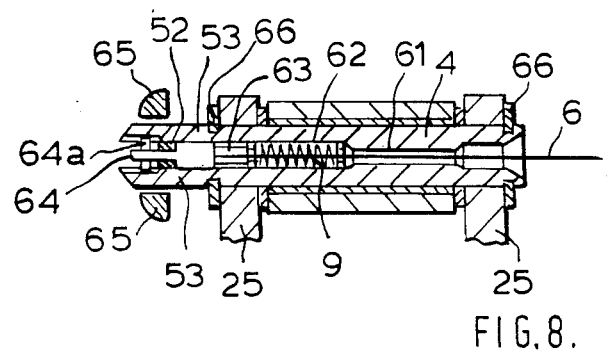
Figure 9:
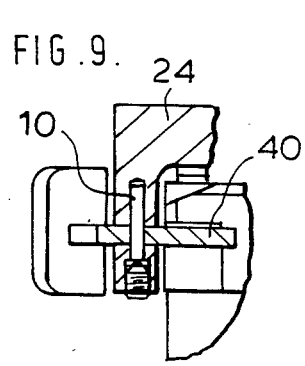
Figure 10:
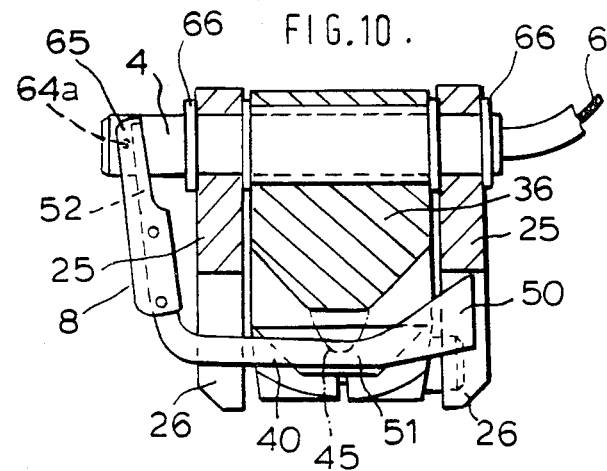

The latch blade 40 as best seen in FIG. 2 is of bellcrank shape in plan, fits slidingly into the slots 26 and is pivoted adjacent the angulation therein on a pivot screw 10 that fits into a vertical anterior bore 34 in one of the cheek plates 25. The head of screw 10 is socketed so that the screw may be tightened by means of an allen key as seen in FIG. 1. Accordingly, the horizontally directed blade 40 is pivoted for rotation towards and away from the sockets 39 about a vertical axis defined by the screw 10. A tip enlargement of the anterior lever 51 of blade 40 in the posterior direction defines a latch head 50 that engages in one or the other of recesses 39 to hold the joint unflexed. It will be appreciated that the blade 40 is reversible and may be pivoted to either of the cheek plates 25 so that the same parts may be used interchangeably for a left or a right leg. A medial lever 52 of the blade 40 fits slidingly between furcations 53 at the medial end of the pin 4. As seen in FIG. 8, the pin 4 is hollow, with a release cable 6 passing through from the lateral end of pin 4, via bore 61 and enlarged counterbore 62 that houses compression spring 9 together with sliding piece 63 that bears against medial lever 52. The cable 6 continues through spring 9, piece 63 and medial lever 52 to which the cable 6 is held by an enlarged end-piece 64 and pin 64a. Accordingly, the medial lever 52 is reciprocable within the slot between furcations 53 by pulling on release cable 6. The outer edge of lever 52 is covered by guard plate 8 that has a rear edge bifurcation 65 to allow passage of the pin 4. Circlips 66 between the cheek plates 25 and the pin 4 retain the pin 4 in position in the assembled knee.

Figure 3:
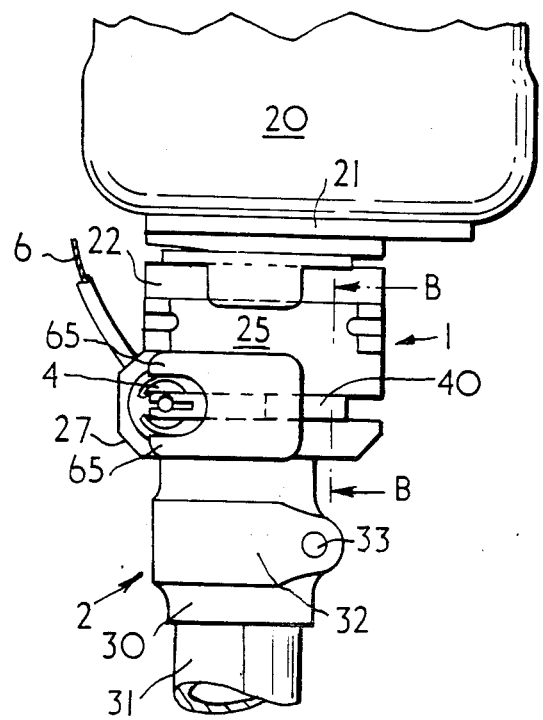
FIGS. 3 and 4 are fragmentary side and front views of a knee unit according to the invention in position in an artificial leg.
Figure 4:
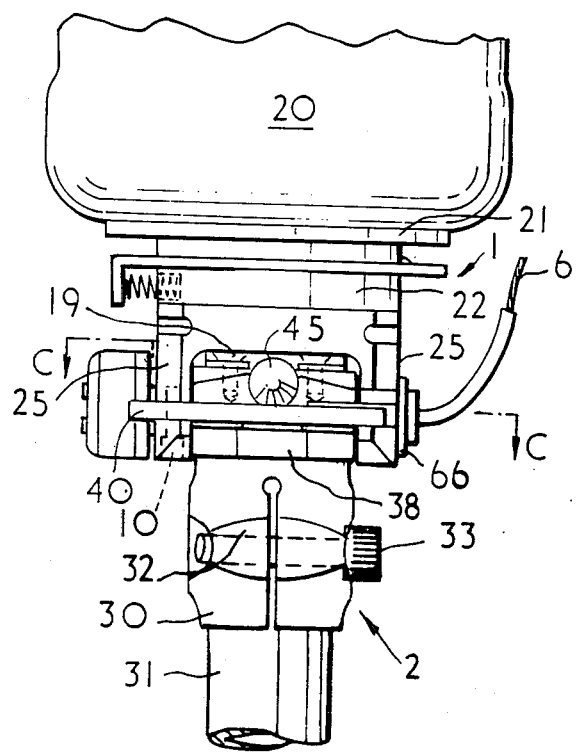
Figure 7:
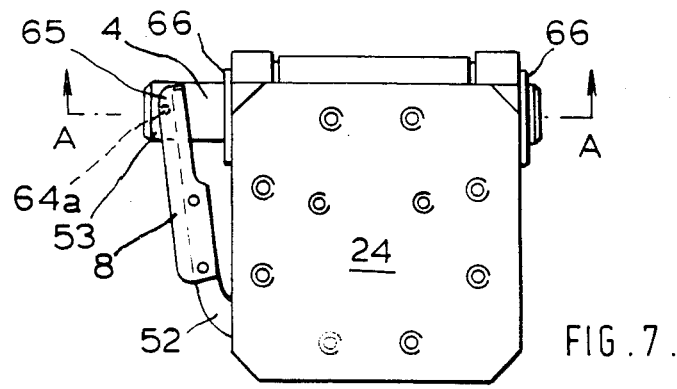
FIGS. 7 to 10 are respectively a plan of the knee joint, a section on the line A—A of FIG. 7, a section on the line B—B of FIG. 3 and a section on the line C—C of FIG. 4.

As the knee joint is moved from the flexed position of FIGS. 5 and 6 towards the extended position of FIGS. 3 and 4 the blade 40 encounters the nose 45 and is rotated so that the latch head 50 rides over and eventually clears the surface 41 and as the knee reaches its extended position is snapped by compression spring 9 into latching engagement with socket 39 of the shin part 1. Travel to the extended positions of FIGS. 3 and 4 also compresses the buffer stop 19 between the lower face of plate 24 and the top face 37 of head 36, and, as previously stated, shims inserted above the buffer stop 19 serve to adjust the buffering action as required. Release is effected by pulling on cable 6 which pivots the blade 40 so as to disengage latch head 50 from the recess 39, after which the joint is free to flex. The posterior position of the pin 4 enables high degree of flexion approaching 180°. Because the blade 40 acts as a pair of levers, the release force required in cable 6 and return force to be provided by compresison spring 9 can be relatively low compared to prior art knee joints where a release cable pulls along the line of action of a locking plunger and this is an advantage for arthritic or geriatric patients who find it difficult or painful to exert more than a minimal force on a release lever (not shown) connected to the other end of the cable 6.

It will be noted that the joint is both of low height and compact but is robust and provides for a high degree of flexion. It may fit inside a one-piece leg cosmesis of foamed plastics material without the foam being damaged in service because, as seen in FIG. 5, the cheek plates 25 serve to push the material of the cosmesis from the gap between the upper and lower assemblies 1, 2 as the joint is unflexed. It readily provides the manual release/self-locking action appropriate to geriatric or arthritic patients.

I claim:

1. A knee joint for a leg prosthesis, comprising:
   an upper member including a horizontal face;
   a lower member including a horizontal face;
   a pin pivotally connecting said upper and lower members, said pin being positioned at a posterior location of said joint;
   a latch member pivoted to one of said members for rotation about a vertical axis;
   means defining a recess in the other of said members in which said latch member releasably locks to hold said joint in its extended position;
   said upper member including depending medial and lateral portions defining cheeks and portions of said lower member defining a head, said head being received between said cheeks; and
   means in the anterior edge of each cheek defining a slot and said latch member comprising a generally bell-cranked blade defining an anterior lever including a latch head and a medial/lateral lever, said blade fitting into said slots and being pivoted to one of said cheeks so that said anterior lever spans between said cheeks with the latch head on said anterior lever fitting into said recess, said joint further comprising a cable release for actuating said medial/lateral lever.

2. A joint according to claim 1, wherein adjoining horizontal faces of said upper and lower members are planar and a pad of elastomeric material is attached to one of said planar surfaces to serve as an extension stop buffer.

3. A joint according to claim 1, wherein said lower member has a nose of wear resistant material at an anterior position on its head that cams said blade to its release position as said joint moves to the extended position, said blade disengaging from the nose as the extended position is reached to snap into the recess.

4. A joint according to claim 1, wherein means in said pin defines an axial bore having an enlarged portion, said release cable passing to a posterior portion of said medial/lateral lever through said axial bore and a compression coil spring housed in said enlarged portion of said bore urging said blade towards its locking position.

5. A joint according to claim 4, wherein furcations are formed at an end of said pin and said posterior portion of said medial/lateral lever slides between said furcations during travel of said blade between release and locking positions.

6. A joint according to claim 5, wherein said lower member is socketed to fit onto the end of a pylon tube.

* * * * *